United States Patent [19]

Jacobsen et al.

[11] Patent Number: 5,556,263

[45] Date of Patent: Sep. 17, 1996

[54] VOLUMETRIC PUMP AND VALUE

[75] Inventors: Stephen C. Jacobsen; Clark C. Davis, both of Salt Lake City, Utah

[73] Assignee: Sarcos Group, Salt Lake City, Utah

[21] Appl. No.: 469,473

[22] Filed: Jun. 6, 1995

Related U.S. Application Data

[62] Division of Ser. No. 157,693, Nov. 23, 1993.

[51] Int. Cl.$^6$ .................................................. F04B 7/00
[52] U.S. Cl. ............................................. 417/490; 417/520
[58] Field of Search ............................... 417/415, 490, 417/499, 510, 511, 520; 92/168

[56] References Cited

FOREIGN PATENT DOCUMENTS 1328918  7/1961  France ................................ 417/520

*Primary Examiner*—Peter Korytnyk
*Attorney, Agent, or Firm*—Thorpe North & Western

[57] ABSTRACT

A volumetric pump and fluid control valve system for controlling the flow of fluid which comprises a housing containing an interior cavity, an elongated valve shaft is disposed inside the cavity, and an elongate drive shaft of smaller diameter than the valve shaft connected to one end of the valve shaft. The drive shaft passes through a passage formed in the housing to extend from the cavity to the exterior. A resilient sheet of material having an aperture is disposed in the housing on the exterior side of the passage and the drive shaft passes through the aperture to form a sphincter seal. The drive shaft can be used to move the valve shaft back and forth in a reciprocating motion producing positive and negative pressures causing fluid to flow or merely to stabilize the valve shaft in position. The valve shaft includes two flanges which are spaced apart from one another. The flanges extend at least partially around the circumference of the valve shaft. The drive shaft is disposed in the cavity above the valve shaft and substantially parallel thereto. A tab extends downwardly from the piston sufficiently far to abut either of the flanges when the piston is moved longitudinally a sufficient distance.

1 Claim, 9 Drawing Sheets

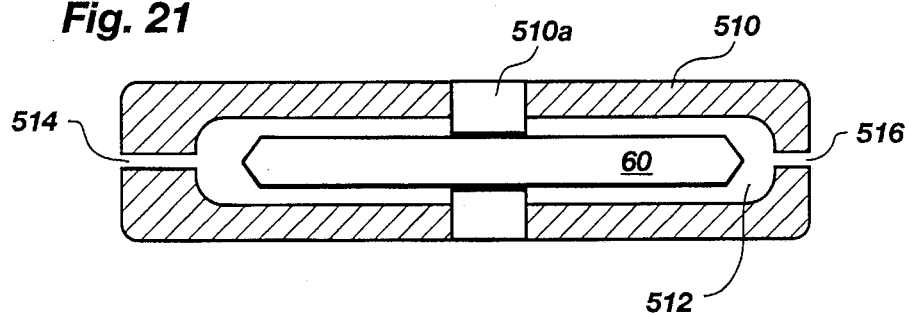
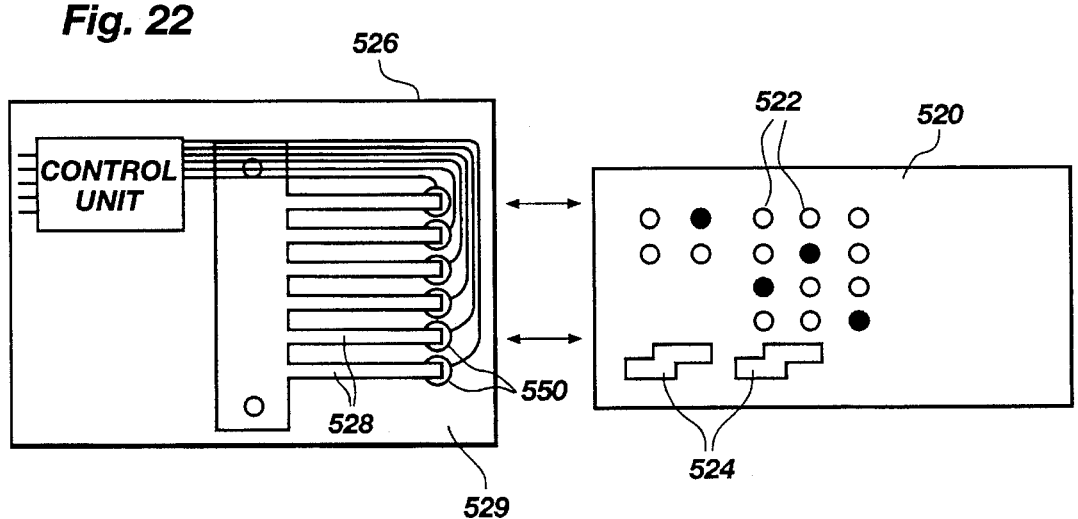
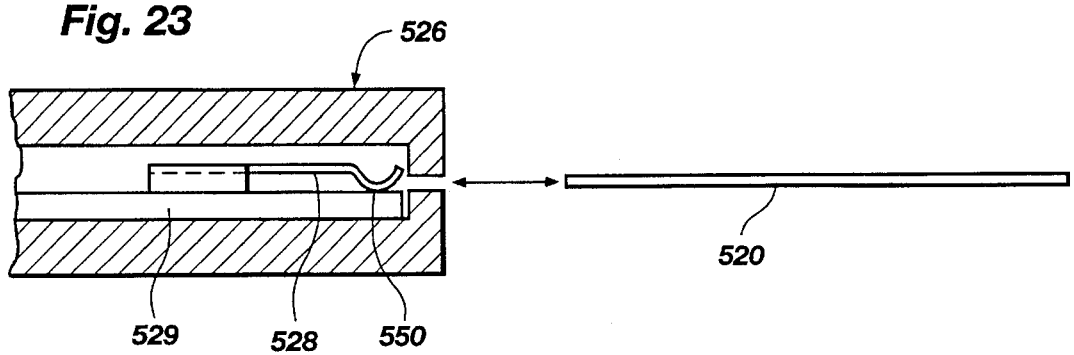

VOLUMETRIC PUMP AND VALUE

This application is a divisional of application Ser. No. 08/157,693, filed Nov. 23, 1993 now issued.

BACKGROUND OF THE INVENTION

This invention relates to a lightweight, inexpensive volumetric pump, suitable for a variety of uses including medical systems such as intravenous (IV) therapy systems and the like.

The intravenous administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently requires the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

SUMMARY OF THE INVENTION

It is an object of the invention to provide a new and improved volumetric pump and valve combination which is especially suitable for use in IV administration sets, other medical systems, and the like.

It is also an object of the invention to provide such a pump and valve combination configured to sweep bubbles from the pump and valve chambers during operation.

It is a further object of the invention to provide such a pump which is easy to manufacture and utilizes low cost parts.

It is another object of the invention to provide such a combined pump and valve design in which tight tolerances are not required.

It is also an object of the invention to provide such a pump which is efficient and reliable.

It is an additional object of the invention to provide such a combined pump and valve which may be readily miniaturized.

It is still another object of the invention, in accordance with one aspect thereof, to provide such a combined pump and valve whose flow rate may be readily changed.

It is a further object of the invention to provide valves, driving mechanisms, control methods, programming methods and apparatus, and pressure detectors suitable for use with the combined pump and valve.

The above and other objects of the invention are realized in a specific illustrative embodiment of a pump and valve combination which utilizes a simple circumferential polymeric seal, or sphincter seal to retain and prevent loss or leaking of the fluid being pumped.

One illustrative embodiment of the invention includes a housing having an interior cavity. An elongate valve shaft is disposed inside the cavity and an elongate drive shaft of smaller diameter than the valve shaft is connected to one end of the valve shaft. The drive shaft passes through a passage formed in the housing to extend from the cavity to the exterior. A resilient sheet of material having an aperture is disposed in the housing on the exterior side of the passage and the drive shaft passes through the aperture to form a sphincter seal. The drive shaft can be used to move the valve back and forth in a reciprocating motion producing positive or negative pressure causing fluid to flow or merely to stabilize the valve shaft in a position or simply not used or removed from the apparatus.

The valve shaft includes two flanges spaced apart from one another. The flanges may extend only particularly around the circumference of the valve shaft or complete around if desired. Although in the later case the bottom of the cavity would need to be lower.

A tab extends downwardly from the drive shaft sufficiently far to abut either of the flanges when the piston is moved longitudinally a sufficient distance.

An inlet conduit passes through the housing and into the cavity near the connection of the valve shaft. A second resilient sheet of material with a second is disposed across the inlet conduit substantially parallel to the first sheet with the first aperture and the second aperture aligned along the drive shaft. The second aperture is larger than the first aperture enabling the drive shaft to pass through the second aperture without forming a sphincter seal, though the second aperture is small enough to form a sphincter seal with the valve shaft when the later passes therethrough.

An outlet conduit passes through the housing into the cavity near the opposite end of the valve shaft to form an inlet conduit. A third resilient sheet of material with a third aperture of approximately the same size as the second aperture is aligned therewith, is disposed across the outlet conduit substantially parallel to the second sheet. The valve shaft selectively passes through the third aperture forming a sphincter seal therewith when passing through it.

The inlet and outlet conduits are attached to a fluid source and a fluid sink respectively.

A variety of valves using sphincter seals and similar mechanisms may be provided to control fluid flow in the pump, among other mechanisms, and electro-mechanical sensors may be provided to detect over- or underpressure of fluid in the pump, or other mechanisms.

BRIEF DESCRIPTION OF THE DRAWINGS

The above and other objects, features and advantages of the invention will become apparent from a consideration of the following detailed description presented in connection with the accompanying drawings in which:

FIG. 21 is a side, cross-sectional view of another embodiment of a seal according to the invention;

FIG. 22 is a top, schematic view of a programming card system for controlling the driving mechanism in the present invention;

FIG. 23 is a side, cross-sectional view of the programming card system of FIG. 22;

DETAILED DESCRIPTION OF THE DRAWINGS

Figure 1:
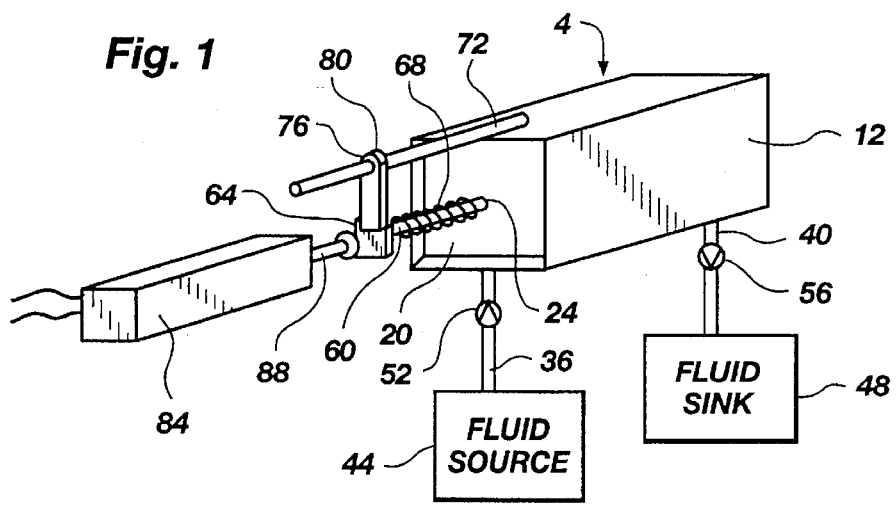
FIG. 1 is a perspective view of a volumetric pump, using a sphincter seal, made in accordance with the principles of the present invention.
Figure 3:
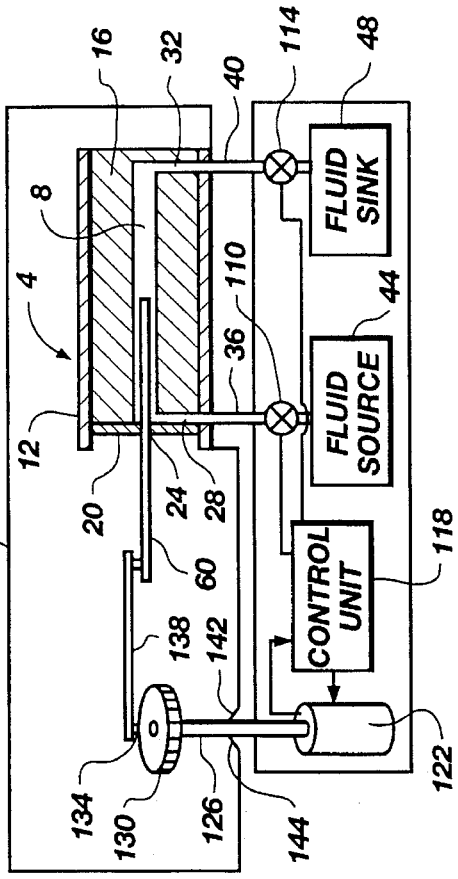
FIG. 3 is a side, cross-sectional, schematic view of another embodiment of a volumetric pump made in accordance with the principles of the present invention.

Referring to FIG. 1, there is shown a perspective view of a volumetric pump made in accordance with the present invention to include a generally elongate housing 4, formed with an elongate cavity 8 therein (refer to FIG. 3 which also shows the housing 4 and the elongate cavity 8). The housing 4 might illustratively be formed with an exterior shell 12 made of metal or hard plastic, and an interior filler 16 disposed against the shell 12, with the cavity 8 formed centrally therein. The filler could similarly be metal or hard plastic.

Disposed in one end of the housing 4 is a resilient sheet of material 20 made, for example, of latex rubber, silicone rubber, or nitrile rubber. The sheet of material 20 fills the end of the housing 4 to prevent communication between the outside of the housing and the cavity 8 except through an aperture 24 positioned in line with the cavity 8.

An inlet duct 28 is formed in the housing 4 generally adjacent to the sheet of material 20, to communicate with the cavity 8, and an outlet duct 32 is similarly formed in the housing to communicate with the cavity at the other end thereof (FIG. 3). Conduits 36 and 40 respectively couple ducts 28 and 32 to a fluid source 44 and a fluid sink 48 (FIG. 1). Check valves 52 and 56 are disposed respectively in conduits 36 and 40 to allow fluid to flow from the fluid source 44 into the cavity 8 and prevent the reverse flow, and to allow fluids to flow from the cavity 8 to the fluid sink 48 and prevent the reverse flow. The fluid source 44 could be any source of fluid which it is desired be pumped to fluid sink 48, such as an IV administration set which includes a bottle of fluid to be administered to a patient, with the fluid source 44 being the bottle and the fluid sink 48 being the patient receiving the fluid. Of course, as will be evident upon further discussion, the fluidic pump of FIG. 1 could be used in a variety of environments.

An elongate shaft or plunger 60 is disposed in the aperture 24 of the sheet of material 20 to extend at least partially into the cavity 8 (FIG. 3) of the housing 4. The shaft 60 may have a circular cross section and have a somewhat smaller circumference than that of the cavity 8 so that the shaft may be moved in a reciprocating fashion back and forth in the aperture 24 and cavity 8. The aperture 24 is preferably shaped similarly to the cross-sectional shape of the shaft 60 and is preferably the same or slightly smaller in size in order to completely surround and grip the shaft to form a sphincter seal and prevent fluid from escaping the cavity 8. As the aperture is formed in the resilient sheet of material 20, the aperture conforms to the shape of the shaft 60 even if their shapes are not identical, though it will be obvious to those skilled in the art that the more the shapes differ the less effective the seal will be.

Disposed on the free end of the shaft 60 is a bumper pad 64 (FIG. 1). A coil spring 68 is disposed about that portion of the shaft 60 which is outside of the housing to provide a bias force against the bumper pad 64 to urge the shaft outwardly from the housing.

A support rod 72 is mounted on the top of the housing 4 and extends forwardly therefrom, and a stopper finger 76 is slidably mounted on the rod 72 so that it may be slid forwardly or rearwardly along the rod. A set screw 80 is provided in the stopper finger 76 to allow for setting or fixing the position of the stopper finger on the rod. Stopper finger 76 extends downwardly to a position in the pathway of possible movement of the bumper pad 64 to prevent the bumper pad and thus the shaft 60 from moving outwardly from the housing 4 beyond the location of the stopper finger. FIG. 1 shows the bumper pad 64 resting against the lower and of the stopper finger 76 to illustrate that the bumper pad 64 and shaft 60 are prevented from moving any further outwardly from the housing 4. The setting of the stopper finger 76 by means of the set screw 80 determines the stroke or excursion of movement of the shaft 60 within the cavity 8 of the housing 4.

A driving mechanism 84, such as a solenoid, is positioned in front of the housing 4 so that a solenoid drive core 88 extends toward the bumper pad 64 as shown. When the drive mechanism 84 is activated (for example by applying an electrical current to a solenoid), the driver core 88 is caused to move towards the bumper pad 64, engage it and move the bumper pad and the shaft 60 toward the housing 4 so that the shaft moves further into the cavity 8 of the housing. When the drive mechanism 84 is deactivated, the drive core 88 retracts into the drive mechanism 84 allowing the coil spring 68 to urge the bumper pad 64 and thus the shaft 60 outwardly from the housing until the bumper pad contacts the stopper finger 76. Alternative activation and deactivation of the drive mechanism 84 will thus result in the shaft 60 being reciprocated within the cavity 8 of the housing 4.

In operation, when the shaft 60 is moved further into the cavity 8, any fluid within the cavity is forced into the conduit 40 and through the check valve 56 to the fluid sink 48. When the shaft is allowed to retract or move outwardly of the cavity 8, a negative pressure is created in the cavity, causing fluid to be drawn from the fluid 44 through the check valve 52 and into the cavity. The continued reciprocation of the shaft 60 thereby provides for pumping fluids from the fluid source 44 to the fluid sink 48.

One advantage to the pumps shown in FIGS. 1 and 3 is that the shapes of the plunger and cavity cause gas bubbles to be swept out of the cavity with each stroke of the plunger, instead of accumulating in the cavity, especially around the seal made in the sheet 20. This allows for greater volumetric accuracy in the pumping action.

Figure 1A:
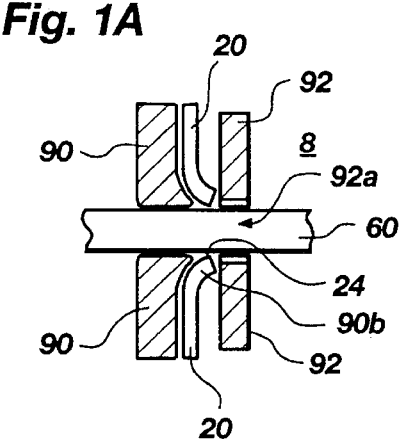
FIG. 1A is a fragmented, side, cross-sectional view of a preferred embodiment of front and rear supports to prevent degradation and waffling of the sphincter seal.

FIG. 1A shows a fragmented, side, cross-sectional view of the shaft 60, the aperture 24 in the resilient sheet 20, with the addition of forward and rear seal supports 90 and 92. The supports 90 and 92 allow for greater positive or negative fluid pressure in the cavity 8 by supporting the sheet.20 at the aperture 24 so that it does not distend with the movement of the shaft 60 into the cavity (to thus stretch and degrade the resilient material and damage the seal), or collapse with the movement of the shaft 60 out of the cavity (to further degrade the material and damage the seal). Greater fluid pressure in the cavity exacerbates the problems of distending and collapsing the sheet 20, which the supports 90 and 92 help prevent.

The rear support 92 preferably comprises an inflexible flat plate with an aperture 92a formed therein. The aperture 92a is preferably similar in shape and slightly larger in size than the shaft 60 to allow free movement of the shaft therein, and is located close to the sheet 20. During movement of the shaft 60 into the cavity 8, the friction of the shaft 60 against the sheet 20 at the aperture 24 tends to cause the latter to distend toward the cavity 8. The sheet 20 at the aperture 24, however, contacts the support 92 before distending enough to damage the material or loosen the seal.

Like the support 92, the support 90 preferably comprises a plate with an aperture 90a formed therein, but also a lip 90b around the aperture, extending toward the cavity 8. The lip is preferably shaped to approximate the shape of the sheet 20 at the aperture 24 after the shaft 60 has been inserted therein. During movement of the shaft 60 out of the cavity 8, the fluid pressure in the cavity and the friction of the shaft 60 against the sheet 20 at the aperture 24 tend to cause the aperture to collapse upon itself in a direction away from the cavity 8. The support 90, however, prevents collapsing and maintains the desired position of the sheet 20 at the aperture 24 during withdrawal of the shaft 60 from the cavity 8. The support 90 also bears a large amount of fluid pressure from the cavity 8, relieving somewhat the pressure on the sheet 20.

Figure 1B:
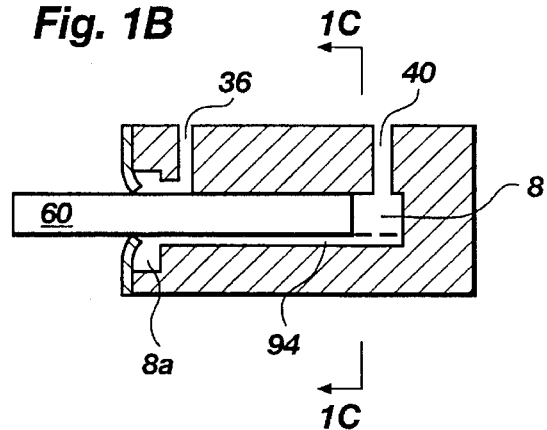
FIG. 1B is a fragmented, side, cross-sectional view of another embodiment of a volumetric pump made in accordance with the principles of the present invention.
Figure 1C:
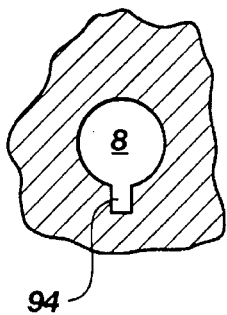
FIG. 1C is a fragmented end view along line 1C—1C of FIG. 1B.

FIG. 1B shows another pump similar to that shown in FIG. 1 except that the cavity 8 is close to the shape and size of the plunger 60 in cross section except for a trough 94 which runs adjacent the length of the cavity. Also, the cavity 8 is enlarged in an area 8a around the sphincter seal to be in fluid communication with an inlet conduit 36, such that fluid can flow from the conduit 36 into the cavity 8 and trough 94 even when the plunger 60 is inserted into the cavity.

The pumping action in the embodiment of FIG. 1B is the same as in FIGS. 1, and the cavity 8 shape and size with trough 94 helps to further eliminate bubbles from low-flow areas in the cavity.

Figure 2:
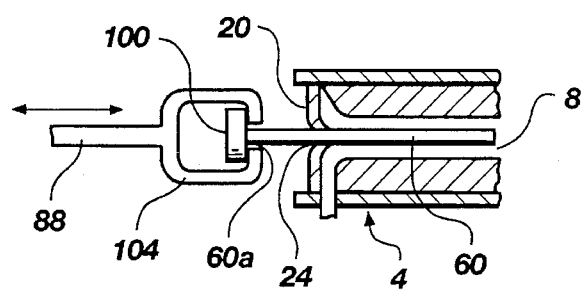
FIG. 2 is a fragmented, side, cross-sectional view of one embodiment of a drive/pump shaft interface for stopping the pumping action if too little or too much pressure is created in the pump cavity.

FIG. 2 shows a fragmented, side, cross-sectional view of one embodiment of a drive/pump shaft interface for terminating the pumping action if too little or too much pressure is created in the pump cavity 8. The shaft 60 is slidably disposed in the cavity 8 and to extend outwardly through an aperture 24 in the resilient sheet of material 20 to terminate at a free end 60a. Disposed on the free end 60a of the shaft 60, which is made of a ferro-magnetic material, is a magnet cap 100. The magnet cap 100 is magnetically attracted to the free end 60a of the shaft 60 to remain in place until a force greater than the magnetic attraction force pulls the magnet cap from off the free end 60a of the shaft 60. Formed on the end of a driver core 88 is a bracket 104, made of a ferromagnetic material, which branches into two fingers outwardly and then behind the magnet cap 100, to positions in contact with a rear surface of the magnet cap. The two fingers of the bracket 104 are magnetically attracted into contact with the magnet cap 100 and will remain in contact until a force greater than the magnetic force of attraction is applied to the bracket in a direction toward the housing 4.

With the structure shown in FIG. 2, the pumping action of movement of the shaft 60 in the cavity 8 will be stopped if a resistance force to movement of the shaft is encountered either in pushing the shaft further into the cavity 8 or pulling the shaft outwardly of the cavity. In particular, if the resistance force to pulling the shaft 60 outwardly of the cavity 8 exceeds the force of attraction of the magnet cap 100 to the free end 60a of the shaft, the magnet cap will be pulled from off the free end by the bracket 104, and the pumping action will stop. Likewise, if the resistance force to pushing the shaft 60 further into the cavity 8 exceeds the force of magnetic attraction of the bracket 104 to the magnet cap 100, then the bracket will be pushed free from contact with the magnet cap and, again, the pumping action will stop. The advantage of this arrangement is that unexpected resistance to pumping, such as a clogged inlet or a clogged outlet, or other clogging in the fluid pathway, will result in the pumping action being stopped. The stopping of the pumping action could also be used to alert the pump user of a problem in the fluid pathway.

FIG. 3 is a side, cross-sectional, schematic view of another embodiment of a volumetric pump in which the same housing structure 4 as that of FIG. 1 is employed. In this case, however, valves 110 and 114, disposed respectively in conduits 36 and 40, are not check valves as in FIG. 1, but rather are controlled by a control unit 118. The valves 110 and 114 still control the flow of fluid from a fluid source 44 to the cavity 8 and from the cavity 8 to a fluid sink 48, but this is all done under control of the control unit 118.

The control unit 118 also controls operation of an electric motor 122 whose drive shaft 126 is coupled to a drive wheel 130. As the motor 22 operates to rotate the drive shaft 126, the wheel 130 is rotated. A drive nipple 134 is mounted near the perimeter of the drive wheel 130 and is pivotally coupled to one end of a drive shaft 138 which, in turn, is pivotally coupled at its other end to the free end of the pump shaft 60. As the drive wheel 130 is caused to rotate, the drive shaft 138 is caused to reciprocate back and forth and, in turn, cause the shaft 60 to reciprocate in the cavity 8.

A second housing 140 is provided in the preferred embodiment around the housing 4, pump shaft 60, drive shaft 138, drive wheel 130, and a portion of the drive shaft 126, to seal the components from outside contamination or interference. The housing 140 preferably comprises rigid material such as steel or plastic except around the drive shaft 126, where it comprises a sheet of resilient material 142, similar to the sheet 20, with an aperture 144 formed therein to create a sphincter seal on the drive shaft 126 similar to the seal of the sheet 20 around the pump shaft 60. However, in the case of the drive shaft 126, the sheet 142 at the aperture 144 seals the drive shaft 126 during rotational, rather than reciprocal, movement.

In operation, the control unit 118 causes the motor 122 to operate and rotate, with the angular position of the drive shaft 126 being fed back to the control unit. Based on the angular position of the drive shaft 126 and thus the drive wheel 130, the control unit will cause valves 110 and 114 to alternately open and close to allow fluid to flow from the fluid source 44 into the cavity 8 on the withdrawal stroke or movement of the shaft 60, and allow fluid to flow from the cavity 8 to the fluid sink 48 on the pump stroke of the shaft 60. In effect, more direct control of the opening and closing of the valves 110 and 114 is provided to ensure more effective pumping of fluid from the fluid source 44 to the fluid sink 48 by preventing free flow caused when both valves are open at the same time (which might occur, for example, if the fluid source were an IV bag and IV bag was squeezed). The control unit 118 might illustratively be any conventional microprocessor used for controlling operation of electrical equipment.

Figure 4:
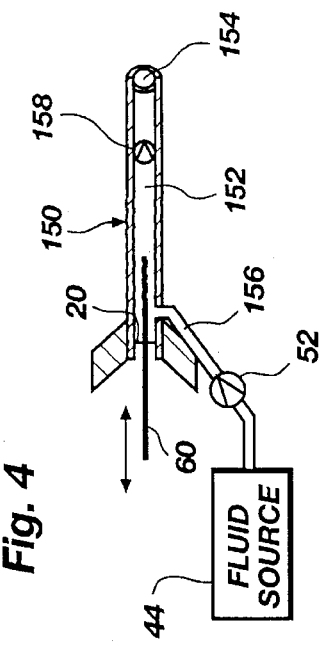
FIG. 4 is a side, cross-sectional view of a volumetric pump made in accordance with the principles of the present invention, incorporated in a hypodermic needle.

FIG. 4 shows a side, cross-sectional view of a volumetric pump according to the invention, incorporated into a hypodermic needle 150. The embodiment of FIG. 4 may be used, for example, to pump medication directly into a patient's bloodstream without the need for intervening tubes and the like.

The needle 150 has an elongate interior cavity 152 and an open outlet end 154. A resilient sheet of material 20 is disposed over the opposite end of the needle, and a shaft or plunger 60 is disposed through an aperture in the sheet 20 for movement inwardly and outwardly of the cavity 152, in the same manner as previously described with regard to FIGS. 1 through 3.

An inlet conduit 156 extends through the side of the needle 150 into the cavity 152 for supply of a fluid into the cavity from a fluid source 44. A valve 52, which may be a mechanical check valve or electronically controlled valve as have been previously described, is located in the inlet conduit 156 and allows fluid to flow from the fluid source through the inlet conduit to the cavity 152, while preventing flow in the opposite direction. A similar valve 158 is provided in the cavity 152 forwardly of the shaft 60 to allow forward movement of fluid from the shaft to the outlet end 154 of the needle, while preventing flow in the opposite direction.

In operation, when the shaft 60 is moved rearwardly (outwardly) from the cavity 152 under power of a drive means (not shown but described in this specification or other suitable drive means), it creates a negative pressure in the cavity 152, causing fluid from the fluid source 44 to enter the inlet conduit 156 and pass through the valve 52 into the cavity 152. When the shaft 60 reverses direction and moves forwardly (inwardly) into the cavity 152, it creates a positive pressure that pushes the fluid in the cavity through the valve 158 out the outlet end 154 of the needle and into, for example, the patient in which the needle is inserted.

With the repetition of this process, medication or other fluid can be steadily pumped directly into a patient.

Figure 5:
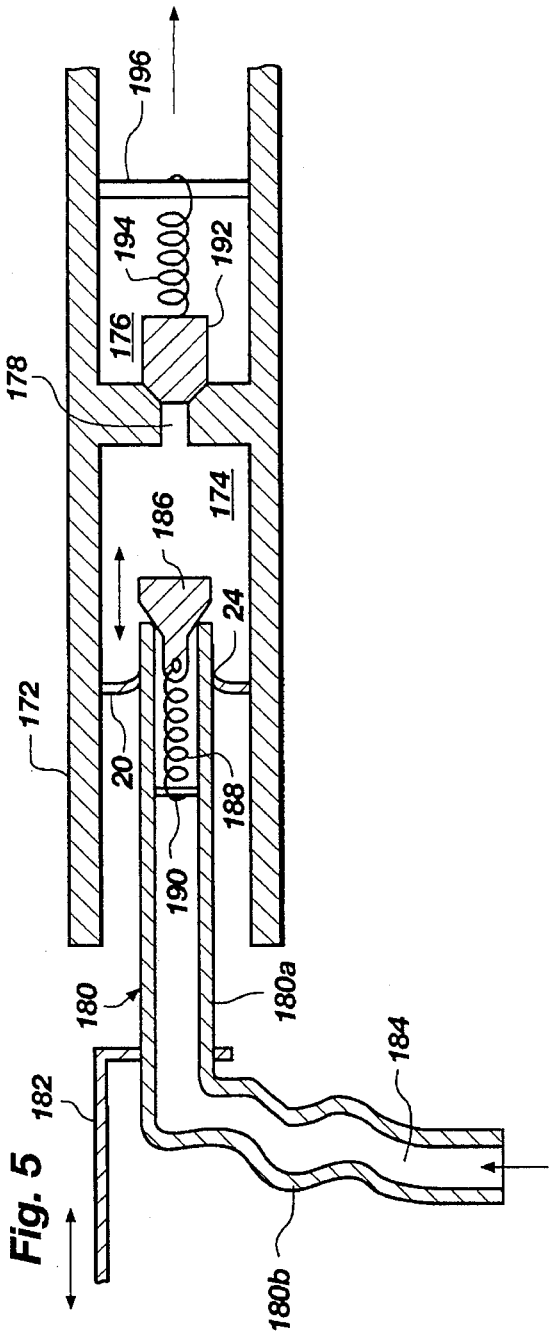
FIG. 5 is a side, cross-sectional view of still another embodiment of a volumetric pump made in accordance with the principles of the present invention.

FIG. 5 is a fragmented, side, cross-sectional view of another embodiment of a volumetric pump in accordance with the invention. The elongate housing 172 of the pump contains two interior cavities: an inlet cavity 174 at the rear of the housing and an outlet cavity 176 at the front of the housing. A passage 178 provides communication between the two cavities. A sheet of resilient material 20 is disposed in the inlet cavity 174, closing off a portion of the cavity such that the only openings to it are an aperture 24 in the sheet 20 and the passage 178.

An elongate pump shaft or plunger 180 is disposed in the inlet cavity 174 through the aperture 24 forming a sphincter seal as previously described. A drive bracket 182, driven by suitable drive means (not shown), is connected to the pump shaft 180 and moves the latter back and forth in reciprocal movement inwardly and outwardly of the inlet cavity 174. As in previously-described embodiments, the drive bracket 182 does not move the pump shaft 180 so far as to pull it out of the sphincter seal.

A forward portion 180a of the pump shaft 180, which extends through the sphincter seal formed by the resilient sheet 20 and aperture 24 and which is connected to the drive bracket 182, is rigid in the preferred embodiment. A rear portion 180b of the pump shaft is flexible. One end of the rear portion 180b attaches to the forward portion 180a, while the other end attaches to a fluid source (not shown). The rear portion 180b of the pump shaft is flexible to accommodate the reciprocating movement of the forward portion of the shaft while enabling it to remain connected to a stationary fluid source.

An inlet conduit 184 is formed in the pump shaft 180 for supplying fluid from the fluid source into the inlet cavity 174. A plug 186 is disposed at the end of the inlet conduit 184 in the inlet cavity. The plug is connected by a coil spring 188 to a pin 190 fixed in the interior of the inlet conduit 184, the arrangement being configured such that the spring urges the plug against the opening of the inlet conduit 184 absent other forces.

In the outlet cavity 176, a second plug 192 is urged against the passage 178 under force of a coil spring 194 attached at one end to the plug 192 and at the other to a pin 196 fixed in the outlet cavity. Absent other forces, the plug 192 closes communication via the passage between the inlet cavity 174 and the outlet cavity 176.

In operation, when the drive bracket 182 moves the pump shaft 180 rearwardly (outwardly) from the inlet cavity 174, the movement creates a negative pressure in the cavity since it is closed off by the plug 192 and the sheet 20. This negative pressure creates a pressure differential between the cavity and the fluid-filled inlet conduit 184, which, in the preferred embodiment, overcomes the force of the spring 188 and forces the plug 186 off its seat on the end of the inlet conduit, causing fluid to flow from the inlet conduit into the cavity 174.

When the pump shaft 180 reverses direction and moves forwardly (inwardly) into the cavity 174, it creates a positive pressure in the cavity 174 which pushes the plug 186 back on its seat with the assistance of the spring 188. The positive pressure also overcomes the force of the spring 194 holding the plug 192 against the passage 178, forcing the plug back and allowing fluid to flow from the inlet cavity 174 into the outlet cavity 176, and from there to, for example, a fluid sink or patient.

When the shaft's movement again reverses, in addition to forcing the plug 186 from its seat on the inlet conduit 184, it causes the plug 192 to again be seated against the passage 178. During forward movement of the shaft, therefore, the plug 192 is unseated while the plug 186 is seated. During rearward movement of the shaft, the plug 192 is seated while the plug 186 is unseated.

Figure 6:
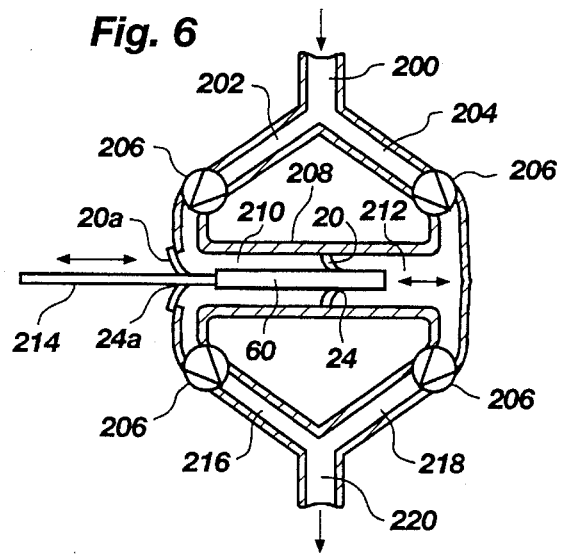
FIG. 6 is a side, cross-sectional view of a further embodiment of a volumetric pump made in accordance with the principles of the present invention.

FIG. 6 is a fragmented, side, cross-sectional view of a further embodiment of a volumetric pump according to the invention. In this embodiment, a fluid inlet passage 200 formed of suitable tubing or piping leads from a fluid source (not shown) into dual inlet conduits 202 and 204, each having a check valve 206 for prevention of backward flow. The inlet conduits are connected to opposite ends of an elongate housing 208 which contains interior cavities 210 and 212 which, in turn, are separated by a sheet 20 of resilient material disposed in the housing. The inlet conduit 202 leads into the cavity 210, while the inlet conduit 204 leads into the cavity 212.

An elongate pump shaft 60 is disposed within the two cavities and through an aperture 24 in the sheet 20, forming a sphincter seal as previously described. A drive shaft 214 attaches to one end of the pump shaft 60 to drive the pump shaft back and forth within the cavities 210 and 212 and through the sheet 20. The drive shaft 214 is powered by any suitable drive means apparent to those skilled in the art in light of this disclosure.

A resilient sheet of material 20a, having an aperture 24a is disposed at one end of the housing 208, through which the drive shaft 214 passes, forms a sphincter seal as previously described.

Outlet conduits 216 and 218 lead out of the cavities 210 and 212, respectively, into a combined fluid outlet passage 220. Like the inlet conduits, each outlet conduit 216 and 218 has a check valve 206 for prevention of backward flow of fluid.

In operation, when the drive shaft 214 moves the pump shaft 60 more into the cavity 210 and out of the cavity 212, a negative pressure is created in the cavity 212, drawing fluid from the inlet conduit 204 into the cavity 212. At the same time, a positive pressure is created in the cavity 210, pushing the fluid contained therein into the outlet conduit 216 and fluid outlet 220.

The valves 206 prevent fluid from flowing in the conduits in any direction but from the fluid inlet 200 toward the fluid outlet 220.

When the pump shaft 60 moves more into the cavity 212 and out of cavity 210, a negative pressure is created in the cavity 210, drawing fluid from the inlet conduit 202 into the cavity 210. At the same time, a positive pressure is created in the cavity 212, pushing the fluid contained therein into the outlet conduit 218 and fluid outlet 220.

Figure 6A:
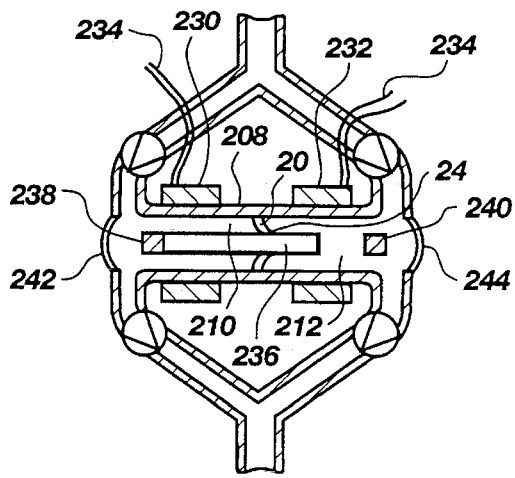
FIG. 6A is a side, cross-sectional view of an embodiment of a volumetric pump similar to that illustrated in FIG. 6, but with a different drive system.

FIG. 6A is a side, cross-sectional view of an embodiment of a volumetric pump similar to that illustrated in FIG. 6, but with a different drive system which eliminates the need for a drive shaft entering the housing. In FIG. 6A, drive coils 230 and 232 are disposed around the cavities 210 and 212, respectively, each coil comprising in the preferred embodiment a series of conductive wires wrapped around the housing 208 defining the cavities. Wires 234 connect the coils to sources of electrical current (not shown).

A pump shaft 236, disposed in the cavities 210 and 212 and through an aperture 24 in sheet of material 20, is preferably constructed of ferro-magnetic or permanent magnet material. When the coil 230 is supplied electrical current through the wires 234, it creates a magnetic field which draws the pump shaft 236 into the cavity 210, as will be apparent to those skilled in the art, until it reaches a fixed permanent magnet 238. In the preferred embodiment, the fixed magnet 238 serves to keep the shaft in position without assistance from the coil 230. Electrical current to the coil 230, therefore, is supplied only momentarily to initially draw the shaft into the cavity 210.

Similarly, when the coil 232 is momentarily energized, it creates a magnetic field which, in the preferred embodiment, overcomes the force of the magnet 238 against the shaft 236 and draws the shaft into the cavity 212 until it reaches a fixed permanent magnet 240, which keeps the shaft in position.

The selective energizing of the coils 230 and 232 thus moves the shaft in a reciprocating movement, pumping fluid similarly as in the embodiment of FIG. 6.

FIG. 6A further shows diaphragms 242 and 244 made of resilient material located at the ends of the housing 208. The diaphragms have some give in them and each bows outwardly when the shaft moves toward it with sufficient force, creating positive pressure in the cavity; for example, diaphragm 242 bows outwardly when the shaft moves into cavity 210. Likewise, each diaphragm moves inwardly when the shaft moves away from its corresponding cavity, creating a negative pressure. The diaphragms lessen the pressure in the cavities caused by movement of the shaft, allowing the shaft to move quickly from one side to the other without power loss in the drive coils 230 and 232 in cases where the inlet and/or outlet conduits are long or otherwise restrictive to fluid flow.

As will be apparent to those skilled in the art, the diaphragms can be made more or less compliant depending on the degree to which the pressure caused by shaft movement is desired to be modified. The diaphragms may also be added to other embodiments of the volumetric pump described herein.

Figure 6B:
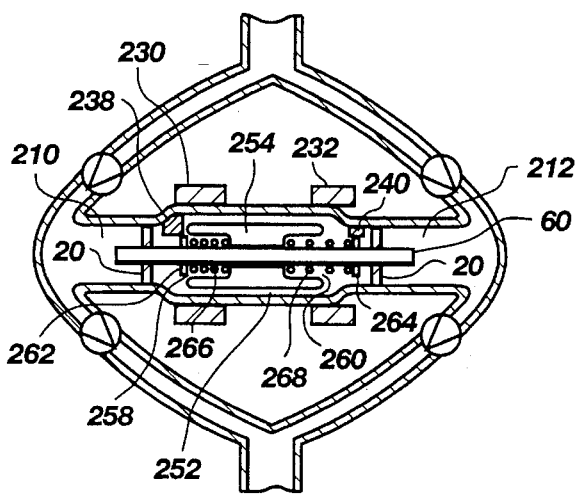
FIG. 6B is a side, cross-sectional view of a further embodiment of a volumetric pump similar to that illustrated in FIG. 6, but with still another drive system.

FIG. 6B is a fragmented, side, cross-sectional view of a further embodiment of a pump similar to that illustrated in FIG. 6, but again with a different drive system. In this embodiment, the housing 208 contains three cavities: the cavities 210 and 212 in their usual positions at the juncture of the inlet and outlet conduits, and an additional interior cavity 252 between the cavities 210 and 212, each cavity separated from the other by a resilient sheet 20 with an aperture through which the pump shaft 60 passes, forming sphincter seals in the manner previously described.

The interior cavity 252 is not used to pump fluid. Rather, it houses a slider 254, preferably cylindrical with a bore through its center and through which the shaft 60 passes. The slider 254 is made of ferro-magnetic or permanent magnet material, disposed coaxially around the pump shaft 60, and has recesses 258 and 260 on either end adjacent the pump shaft. Drive coils 230 and 232 and magnets 238 and 240 are provided to move the slider 254 back and forth in the same manner of moving the shaft 236 back and forth in FIG. 6A. The shaft 60 in FIG. 6B preferably is non-magnetic in order not to be affected by the coils and magnets.

The slider 254 is positioned on and connected to the pump shaft 60 by means of flanges 262 and 264 extending outwardly from the shaft near opposite ends, and coil springs 266 and 268 disposed respectively in the recesses 258 and 260 around the shaft and between the flanges and the slider. The spring 266 urges the slider 254 away from the flange 262, and the spring 268 urges the slider away from the flange 264.

In operation, when the coil 230 is energized (by an electrical current source not shown) it draws slider 254 in the direction of the cavity 210 until it abuts the magnet 238, which holds it in position. The slider applies directional force to the pump shaft 60 through the spring 266, causing the shaft to move into the cavity 210. By its nature, the spring is compliant and will lessen the momentary force of the shaft relative to the slider, slightly lessening the momentary positive pressure in the cavity 210 and negative pressure in the cavity 212. The springs 266 and 268 thus perform the same function as the diaphragms 242 and 244 in FIG. 6A.

When the coil 232 is energized it overcomes the force of the magnet 238 and draws the slider 254 in the direction of the cavity 212 until the slider abuts the magnet 240, which holds the slider in position. The slider 254 applies directional force to the shaft 60 through the spring 268 in the same manner as above described.

Figure 6C:
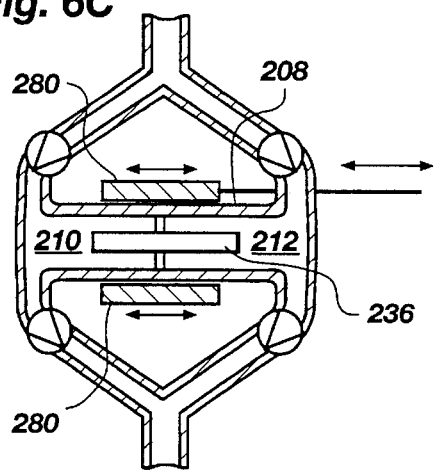
FIG. 6C is a side, cross-sectional view of an additional embodiment of a volumetric pump similar to that illustrated in FIG. 6, again with a different drive system.

FIG. 6C is a fragmented, side, cross-sectional view of a further embodiment of a pump similar in all respects to the embodiment of FIG. 6A except that a pump shaft 236 is driven by a single elongate annular magnet 280 instead of by coils 230 and 232 and magnets 238 and 240. The magnet 280 is slidably disposed around the housing 208 and is moved back and forth by any suitable mechanical means such as the drive mechanisms of FIGS. 1 and 3. As the magnet moves toward the cavity 210, it draws the shaft 236 toward the cavity 210 by magnetic attraction, and as it moves toward the cavity 212, it draws the shaft 236 toward the cavity 212 by magnetic attraction.

Figure 7:
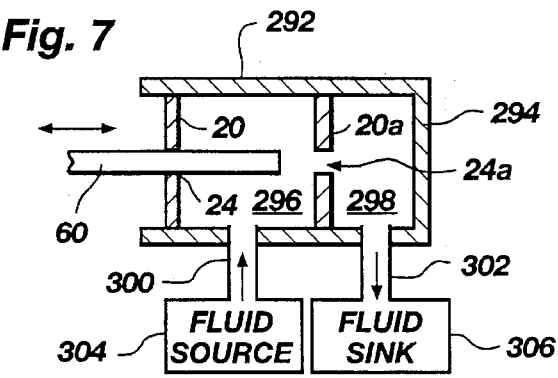
FIG. 7 is a side, cross-sectional view of a valve utilizing sphincter seals, made in accordance with the principles of the present invention.

FIG. 7 shows a side, cross-sectional view of a valve using sphincter seals in accordance with the invention. In this embodiment, an elongate housing 292 is formed of suitable rigid material with a closed end 294. The other end is closed by a resilient sheet of material 20 with an aperture 24 through which a shaft 60 passes, forming a sphincter seal in the manner previously described.

A second sheet of resilient material 20a with an aperture 24a is disposed within the housing 292, dividing it into two cavities 296 and 298, with the aperture 24a serving as a passage therebetween. Unlike previous embodiments of sphincter seals, the shaft 60 passes only selectively, rather than continuously, through the aperture 24a.

A fluid inlet 300 is formed in the housing 292 leading into the cavity 296, and a fluid outlet 302 is formed in the housing leading from the cavity 298. A fluid source 304 is connected to the fluid inlet 300, and a fluid sink 306 is connected to the fluid outlet 302. One or both of the source 304 and sink 306 is pressurized to urge fluid from the source to the sink through the valve.

In operation, when the shaft 60 is withdrawn from the aperture 24a by movement toward the cavity 296, the aperture serves as a passage between the cavities 296 and 298, allowing fluid to flow from the fluid source 304, through the inlet 300, into the cavity 296, through the aperture 24a, into the cavity 298, through the outlet 302, and into the fluid sink 306. When the shaft 60 is placed into the aperture 24a by movement toward the cavity 298, a sphincter seal is formed and communication between the cavities 296 and 298 is blocked, stopping fluid flow. In this manner, the structure of FIG. 7 operates as a valve.

Figure 8:
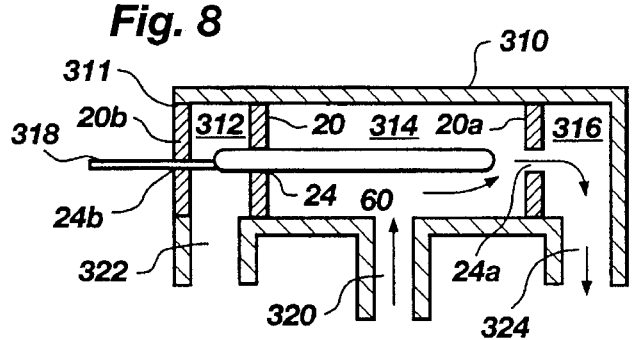
FIG. 8 is a side, cross-sectional view of another embodiment of a valve, also utilizing sphincter seals, made in accordance with the principles of the present invention.

FIG. 8 shows a side, cross-sectional view of another embodiment of a valve using sphincter seals according to the invention, which can be used to switch fluid flow from one destination to another, or stop flow altogether. In this embodiment, a housing 310 is divided into three interior cavities 312, 314, and 316 by two sheets of resilient material 20 and 20a, each having an aperture 24 and 24a, respectively. An elongate shaft 60 moves back and forth through the cavities and apertures, driven by a drive shaft 318 which passes through an aperture 24b in a sheet of resilient material 20b disposed in an opening 311 in the side of the housing 310, forming a sphincter seal as previously described. An inlet conduit 320 leading from a fluid source (not shown) leads into the middle cavity 314. Outlet conduits 322 and 324 lead out of cavities 312 and 316, respectively, to fluid sinks (not shown). Either the fluid source or fluid sinks, or both, are pressurized to urge fluid from the source to the sinks. The shaft 60 selectively passes through the apertures 24 and 24a, selectively forming sphincter seals and blocking fluid flow between the cavities. The shaft 60 may be made long enough to enable it to pass through both apertures 24 and 24a at the same time, completely blocking fluid flow, or may be made shorter so that it is unable to pass through both apertures at the same time.

In operation, when the shaft 60 moves toward the cavity 312, it passes through the aperture 24, forming a sphincter seal therein and blocking fluid flow between the cavities 312 and 314. At the same time, the shaft 60 comes out of the aperture 24a, opening the aperture and enabling fluid to flow from the inlet cavity 314 into the cavity 316 and through the outlet conduit 324 to the fluid sink. When the shaft 60 moves toward the cavity 316, it passes through the aperture 24a, forming a sphincter seal therein and blocking fluid flow between the cavities 314 and 316. At the same time, the shaft comes out of the aperture 24, opening the aperture and enabling fluid to flow from the inlet cavity 314 into the cavity 312 and through the inlet conduit 322 to the fluid sink. If the shaft has been made long enough, it may be centered in the cavity 314, passing through both apertures 24 and 24a and blocking all fluid flow.

Figure 9:
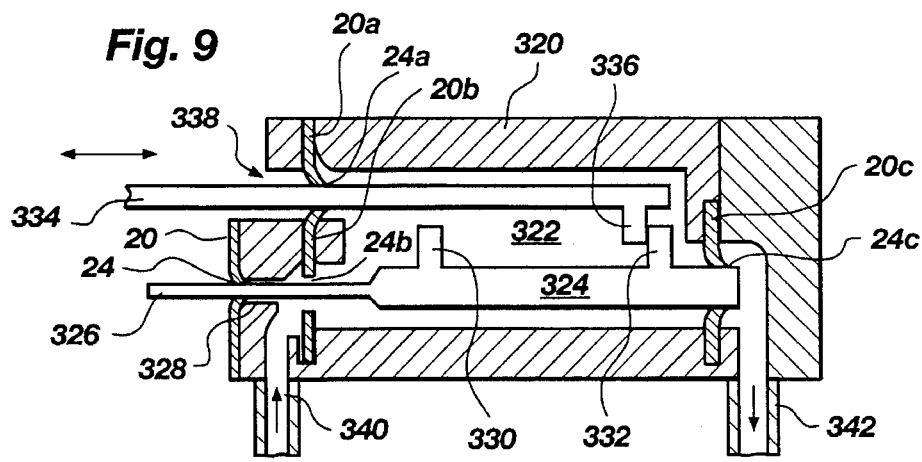
FIG. 9 is a side, cross-sectional view of a spool valve mechanism for use in volumetric pumps of the present invention for controlling the flow of fluid.

FIG. 9 shows a side, cross-sectional view of a spool valve mechanism for controlling the flow of fluid, combined with a pump similar to that of FIG. 3. This embodiment of the invention comprises a housing 320 containing an interior cavity 322 (referred to in the claim as a central hollow). An elongate valve shaft 324 is disposed inside the cavity 322, and an elongate drive shaft 326, of smaller diameter than the valve shaft 324 in the preferred embodiment, is connected to one end of the valve shaft 324. The drive shaft 326 passes through a passage 328 formed in the housing 320 to extend from the cavity 322 to the exterior. A resilient sheet of material 20 having an aperture 24 is disposed on the housing 320 on the exterior side of the passage 328, and the drive shaft 326 passes through the aperture 24 to form a sphincter seal as previously described. The drive shaft 326 can be used to move the valve shaft 324 back and forth in a reciprocating motion, or merely to stabilize the valve shaft 324 in position, or simply not be used or removed from the apparatus.

The valve shaft 324 includes two flanges 330 and 332 spaced apart from one another. The flanges 330 and may extend only partially around the circumference of the valve shaft 324, as shown, or completely around, if desired, though in the latter case, the bottom of the cavity 322 would need to be lowered from what is shown in the drawing.

A piston 334 (referred to in the claim as an elongate plunger) is disposed in the cavity 322 above the valve shaft 324 and substantially parallel thereto. A tab 336 extends downwardly from the piston 334 sufficiently far to abut either of the flanges 330 or 332 when the piston is moved longitudinally a sufficient distance. The piston 334 extends from the cavity 322 to the exterior of the housing 320 through a passage 338 (referred to in the claim as a third opening) formed in the housing 320. A resilient sheet of material 20a (referred to in the claim as a third sheet of resilient material), with an aperture 24a, is disposed across the passage 338, and the piston 334 passes through the aperture 24a to form a sphincter seal as previously described.

An inlet conduit 340 passes through the housing 320 into the cavity 322, near the connection of the valve shaft 324 to the drive shaft 326. A resilient sheet of material 20b (referred to in the claim as a first sheet of resilient material), with an aperture 24b, is disposed across the inlet conduit 340 substantially parallel to the sheet 20, with the apertures 24 and 24b aligned along the drive shaft 326. The aperture 24b is larger than the aperture 24, enabling the drive shaft 326 to pass through the aperture 24b without forming a sphincter seal, though the aperture 24b is small enough to form a sphincter seal with the valve shaft 324 when the latter passes therethrough.

An outlet conduit 342 passes through the housing 320 into the cavity 322 near the opposite end of the valve shaft 324 from the inlet conduit 340. A resilient sheet of material 20c (referred to in the claim as a second sheet of resilient material) with an aperture 24c, of approximately the same size as the aperture 24b and aligned therewith, is disposed across the outlet conduit 342 substantially parallel to the sheet 20b. The valve shaft 324 selectively passes through the aperture 24c, forming a sphincter seal therewith when passing through it.

The inlet and outlet conduits 340 and 342 are attached to a fluid source and a fluid sink, respectively (not shown).

The valve shaft 324 may be made long enough so that when it is centered between the sheets 20b and 20c it passes through both corresponding apertures 24b and 24c and forms sphincter seals with both. Alternatively, the shaft 324 may be made short enough so that when centered between the two sheets 20b and 20c it passes through neither aperture. The valve shaft 324 may be moved back and forth by either the drive shaft 326 attached to suitable drive means, or the piston 334 attached to suitable drive means. If moved by the piston 324, the shaft 324 is moved in the following way: to cut off fluid flow to the outlet conduit 342, the piston 334 is moved toward the outlet conduit 342 until the tab 336 abuts the flange 332 on the valve shaft 324 into and pushes the shaft into the aperture 24c. To cut off fluid flow from the inlet conduit 340, the piston 334 is moved toward the inlet conduit 340 until the tab 336 abuts the flange 330 on the valve shaft 324 into and pushes the shaft into the aperture 24b. The location of the drive shaft 326 through the aperture 24b does not prevent fluid flow from the inlet conduit into the cavity since, as previously noted, the aperture is of a larger diameter than the drive shaft. The positive and negative pressures required to cause fluid flow from the fluid source into the cavity 322, and from the cavity 322 to the fluid sink are produced by the motion of the piston 334, i.e., a pumping action.

FIGS. 10, 11, 12, 13 and 13A show five illustrative embodiments of drive mechanisms which may be used to drive the pump or valve shafts of the present invention.

Figure 10:
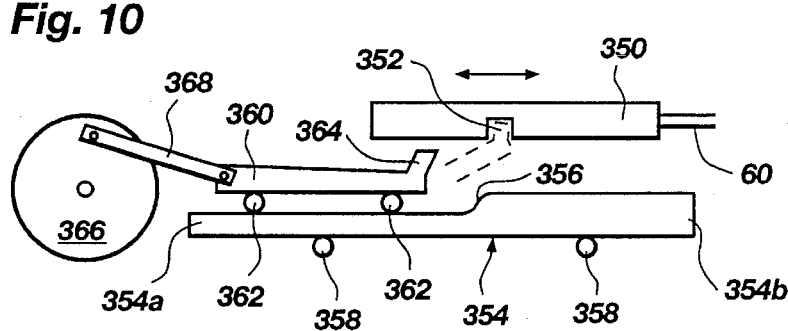
FIGS. 10, 11, 12, 13 and 13A show five illustrative embodiments of drive mechanisms which may be utilized for driving the pump shaft of the volumetric pumps of the present invention.

FIG. 10 shows a side view of a drive mechanism which includes an elongate drive shaft 350 attached to a pump or valve shaft 60, with a notch 352 cut on the bottom of the drive shaft 350. A ramp 354 containing a shoulder 356 is disposed beneath the drive shaft 350. The shoulder 356 divides the ramp into a lower portion 354a and a higher portion 354b. Rollers 358 or other suitable adjustment means are disposed on the underside of the ramp to allow adjusting its longitudinal position to thus vary the stroke length of the pump shaft 60, as described below. A secondary driver 360 is disposed on rollers 362 which rest on the lower portion 354a of the ramp. A tab 364 extends upwardly from the forward end of the secondary driver nearest the shoulder 356. A disc 366 given rotary motion by a motor or other drive means connects to the end of the secondary driver opposite the tab 364 by a rod 368, which is pivotally attached at one end to the disc and at the other to the secondary driver. The rotary motion of the disc 366 moves the secondary driver 360 back and forth in a conventional manner.

In operation, when the secondary driver 360 moves forward, it does not contact the drive shaft 350 until the rollers 362 reach and move up the shoulder 356, forcing the secondary driver 360 upwardly and the tab 364 into the notch 352, causing the drive shaft 350 to be moved forwardly with the secondary driver 360. When the secondary driver 360 moves rearward, it forces the drive shaft 350 rearward by way of the tab/notch connection until the rollers 362 move down the shoulder 356, causing the tab 364 to come out of the notch 352, breaking the connection and stopping movement of the drive shaft 350.

As will be apparent to those skilled in the art, the notch 352 must initially be placed in position to receive the tab 364 when the latter is elevated by the shoulder 356.

The stroke of the drive shaft 350 may be easily adjusted by moving the ramp 354 forwardly or rearwardly. If the ramp is moved rearwardly (with appropriate adjustment of the drive shaft 350 to align the notch), the tab 364 enters the notch earlier in the forward movement of the secondary driver 360, moving the drive shaft farther forward, and correspondingly farther rearward. If the ramp is moved forwardly, the tab enters the notch later in the forward movement of the secondary driver 360, moving the drive shaft a lesser distance forward and a correspondingly lesser distance rearward.

Varying the stroke of the drive shaft 350 adjusts the flow rate of the pump while allowing the driver to be run at a constant rate. Other control or drive mechanisms may be used to accomplish the same end (i.e., adjust the flow rate) such as variable speed drive mechanisms, and variable delay of constant speed drive mechanisms.

Figure 11:
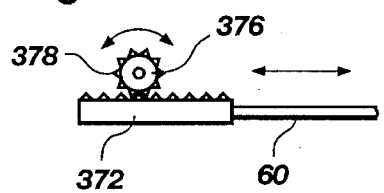

FIG. 11 shows another drive mechanism comprising a pump or valve shaft 60 driven by a drive shaft 372 having teeth 374 on one side. A wheel 376 having teeth 378 spaced circumferentially therearound engages the teeth 374, converting rotary movement of the wheel into longitudinal movement of the drive shaft. The rotary movement of the wheel reverses direction to reverse direction of the drive shaft.

Figure 12:
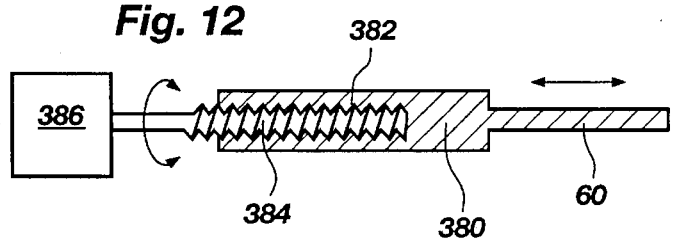

FIG. 12 shows another drive mechanism comprising an elongate drive shaft 380 connected to a pump or valve shaft 60. The drive shaft 380 has a threaded interior recess 382 into which a threaded rod 384 fits. The rod is caused to rotate by a motor 386. Depending on the direction of rotation, the rotational motion of the rod 384 moves the drive shaft 380 back or forth.

Figure 13:
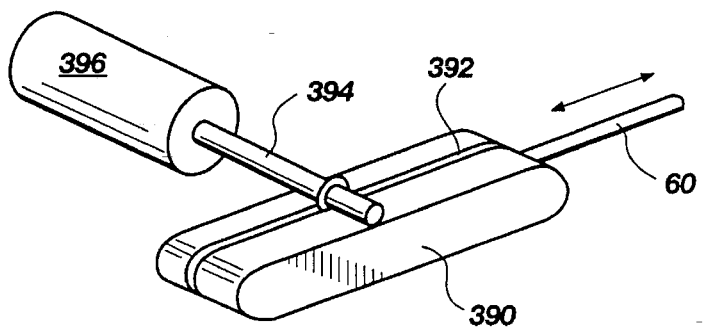

FIG. 13 shows a perspective view of another drive mechanism for a pump shaft 60 attached at one end to a rigid anvil 390 which is oval-shaped in side cross section. A flexible filament 392 made of suitably strong material is wrapped snugly around the anvil, with a loop of the filament wrapped around a drive shaft 394 which is given rotational motion by a motor 396. As the drive shaft rotates to thus move the filament 392, the anvil and thus the pump shaft are caused to move longitudinally, as the drive shaft 394 gathers in and lets out filament 392 to accommodate its rotational movement, the manipulated filament forces the anvil to move in turn.

Figure 13A:
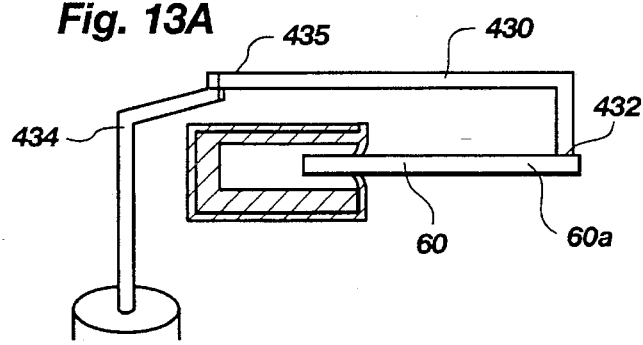

FIG. 13A shows a plunger 60 driven by a drive shaft 430 which is pivotally connected at an outer end 60a to an end 432 of the drive shaft. A crank 434 is pivotally connected to the other end 435 of the drive shaft 430. The crank is rotated by any suitable means, moving the drive shaft 430 in a reciprocating fashion and thus the plunger 60 back and forth in longitudinal movement. Preferably, sphincter seals as described above are formed at fluid interfaces with the components.

Figure 14:
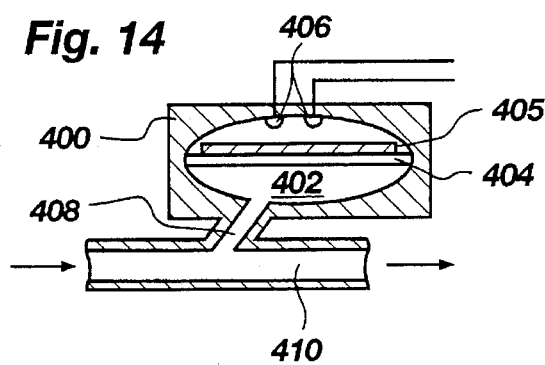
FIG. 14 shows a side, cross-sectional view of a fluid pressure detector for use with volumetric pumps of the present invention, among others.
Figure 15:
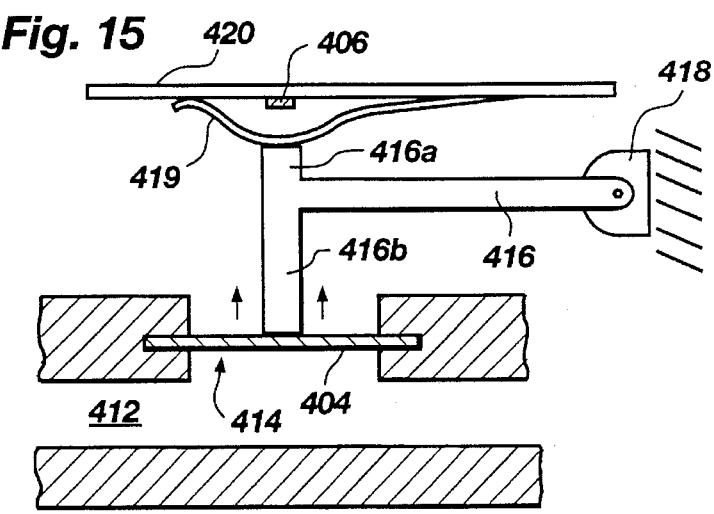
FIG. 15 is a side, cross-sectional view of a further embodiment of a fluid pressure detector.
Figure 16:
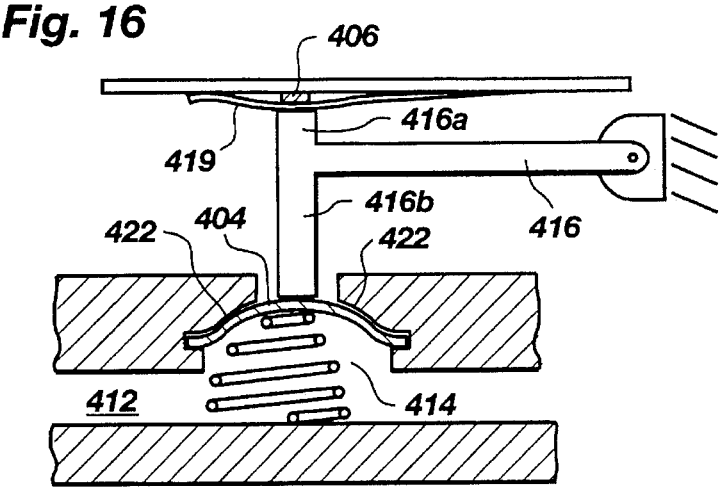
FIG. 16 is a side, cross-sectional view of yet a further embodiment of a fluid pressure detector.

FIGS. 14 through 16 show fluid pressure detectors for use, for example, with the volumetric pumps of the present invention to detect when pressure exceeds a certain level or falls below a certain pressure.

In FIG. 14, a fragmented, side, cross-sectional view, a housing 400 is formed with an interior cavity 402 which is bisected by a conventional compliant diaphragm 404. A flexible conductive disc 405 is disposed on top of the diaphragm 404. Two conductivity sensors 406 are disposed at the top of the cavity 402.

An inlet conduit 408 leads into the cavity 402 from a fluid port 410. As fluid pressure in the port increases, the fluid entering the cavity causes the diaphragm 404 to bow upwardly, until at a predetermined pressure it bows sufficiently far to cause the conductive disc 405 to contact the conductivity sensors 406, electrically shorting them to indicate overpressure in the port.

In FIG. 15, which is also a fragmented, side, cross-sectional view, a fluid port 412 includes an opening 414 through its wall and a diaphragm 404 covering the opening. A T-shaped lever 416, pivotally attached at one end to a stationary point 419, with arms 416a and 416b disposed between and contacting at their ends the diaphragm 404 and a flexible conductive dome contact 418. The dome contact is disposed on a support 420. A conductivity sensor 406 is positioned on the support in alignment with the dome contact.

As fluid pressure in the port 412 increases, the fluid entering the opening 414 causes the diaphragm 404 to bow upwardly, causing, through the arms 416a and 416b of the lever 416, the dome contact 419 to flatten against the support 420. At a predetermined pressure, the diaphragm bows sufficiently far to cause the dome contact 419 to flatten and contact the conductivity sensor 406, indicating overpressure in the port 412.

FIG. 16 shows a fragmented, side, cross-sectional view of a detector for detecting underpressure of fluid in a port 412 (instead of overpressure as in FIGS. 14 and 15). In FIG. 16, an opening 414 is formed with shoulders 422 to limit upward bowing of a diaphragm 404 disposed in the opening. A coil spring 424, together with normal fluid pressure in the port 412, urges the diaphragm 404 against arm 416 which flattens a dome contact 419 to contact a conductivity sensor 406.

If fluid pressure in the port 412 decreases to a predetermined point, the diaphragm 404 begins to flatten toward the port, causing the dome contact 419 to break its connection with the conductivity sensor 406, indicating underpressure in the port.

Figure 17:
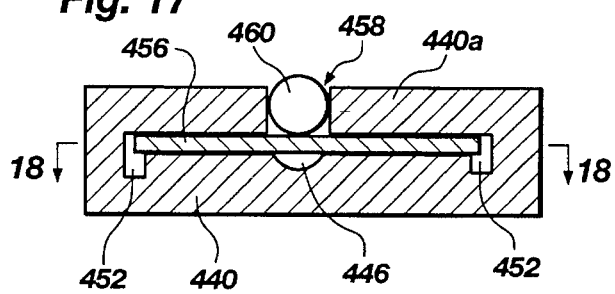
FIG. 17 is a side, cross-sectional view of a ball valve for use with volumetric pumps of the present invention, among others.
Figure 18:
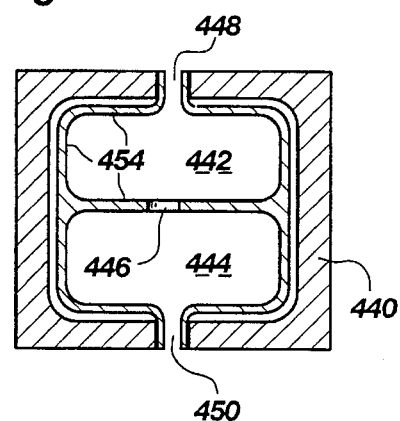
FIG. 18 is a view along line 18—18 in FIG. 17.

FIGS. 17 and 18 show respectively a side, cross-sectional view, and a view taken along lines 18—18 of FIG. 17, a ball valve for use with volumetric pumps of the present invention, among other mechanisms. The ball valve comprises a housing 440 defining therein two adjacent cavities 442 and 444 (FIG. 18) having a passage 446 therebetween. An inlet conduit 448 leads into the cavity 442 from the exterior of the housing, and an outlet conduit 450 leads from the cavity 444 to the exterior of the housing on the opposite side of the housing from the inlet conduit. Walls 454 separate the cavities from the exterior and each other.

A resilient sheet of material 456 (FIG. 17) made of, for example, latex or silicone rubber, is disposed over the cavities and is pressed against the walls 454 by a top portion 440a of the housing 440, sealing the cavities against fluid communication with the exterior or with each other except through the passage 446. An aperture 458 is formed through the top portion 440a of the housing to extend down to the sheet 456 in alignment with the passage 446, and a ball 460 is disposed in the aperture.

In operation, fluid from the inlet conduit 448 flows into the cavity 442. When the valve is in open position (shown in FIG. 17), the fluid continues through the passage 446 into the cavity 444 and out the outlet conduit 450. To close the valve, the ball 460 is pushed down, forcing the sheet 456 to bend downwardly into the passage 446, sealing it from fluid flow. This action stops fluid flow between the cavities.

Figure 19:
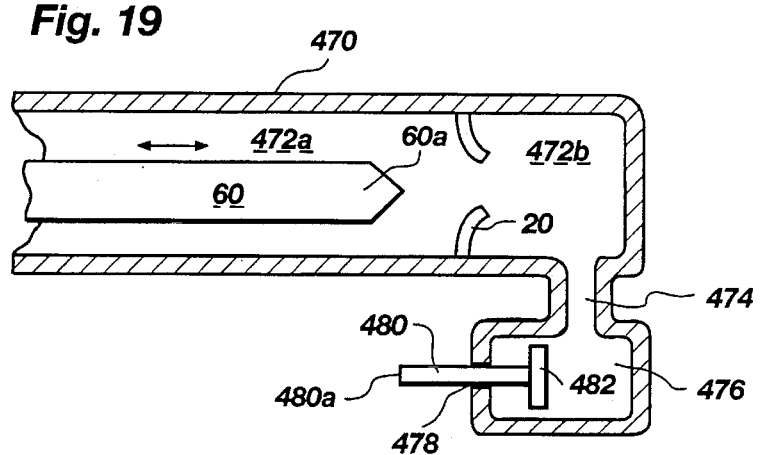
FIG. 19 is a side, cross-sectional view of a plunger bottoming detector according to the invention.

FIG. 19 shows a fragmented, side, cross-sectional view of a plunger "bottoming" detector using the principles of the present invention. A generally elongate housing 470 includes therein an elongate cavity 472 which is divided into adjacent compartments 472a and 472b by a resilient sheet of material 20 containing an aperture which forms a sphincter seal with a shaft or plunger 60 as previously described. A passage 474 connects the compartment 472b with a fluid chamber 476 having an aperture 478 through which is disposed a rod 480 having a piston 482 disposed on one end in the fluid chamber 476. The other end 480a of the rod 480 is preferably operatively connected to a valve or switch (not shown).

The bottoming detector of FIG. 19 is designed to detect when the plunger 60 reaches the end of a stroke, or, alternatively, if it has gone beyond the anticipated reciprocating distance, to take appropriate action. In operation, the plunger 60 moves in reciprocating motion. When its end 60a reaches the sheet 20, it forms a sphincter seal with the sheet. Upon further motion into the (fluid-filled) compartment 472b, fluid is forced from the compartment through the passage 474 and into the fluid chamber 476, increasing pressure in the latter and urging the piston 482 toward the aperture 478, moving the rod 480 and activating the valve or switch to which it is connected. Thus, movement of the plunger 60 beyond the sheet 20 may be detected to alert a user.

Figure 20:
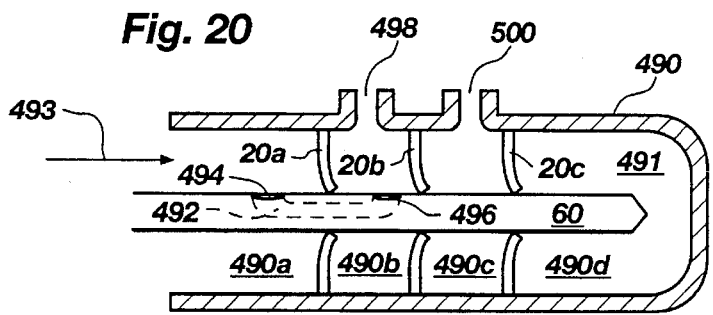
FIG. 20 is a side, cross-sectional view of another embodiment of a valve according to the invention.

FIG. 20 shows another embodiment of a valve according to the invention, comprising a generally elongate housing 490 defining an elongate internal cavity 491 with three sheets of resilient material 20a, 20b, and 20c disposed therein, each sheet containing an aperture for formation of sphincter seals, as previously described. The sheets 20a, 20b, and 20c are spaced from each other, forming four fluid compartments 490a, 490b, 490c, and 490d in the cavity 490. A plunger 60 is disposed in the cavity through the aligned apertures in the sheets, forming sphincter seals therewith. The shaft contains an internal passage 492 running partially along its length with spaced openings 494 and 496 at each end of the passage, in fluid communication with the cavity.

An inlet 498 is formed through the housing wall into the compartment 490b, and an outlet 500 is formed through the housing wall into the adjacent compartment 490c. The openings 494 and 496 are spaced such that when the opening 494 is located in the compartment 490b, the opening 496 is located in the compartment 490c, providing fluid communication from the inlet 498, through the compartment 490b, opening 494, passage 492, opening 496, and compartment 490c to the outlet 500. When the plunger is moved, the openings are moved from their respective positions in the compartments 490b and 490c, blocking communication between the inlet and outlet. This, of course, defines typical valve operation.

The apparatus of FIG. 20 can also be used to direct fluid received, for example, at the left side of the apparatus (indicated by arrow 493) either to inlet 498 (which would become an outlet) or to outlet 500. This would be done by positioning shaft 60 with the opening 496 positioned in compartment 490b so that fluid would flow from compartment 490a through opening 494 and passage 492, out opening 496 into compartment 490b, and out the "outlet" 498. To direct fluid out the outlet 500, the passage 492 would be long enough to allow positioning opening 496 in compartment 490c while opening 494 is still positioned in compartment 490a. Then, with opening 496 positioned in compartment 490c, fluid would flow through opening 494 and passage 492, out the opening 496 into compartment 490c, and then out the outlet 500.

FIG. 21 shows another embodiment of a seal suitable for use in certain applications of pumps or valves of the present invention. In some applications, this seal may be used instead of a sphincter seal as previously described. As in previous embodiments of the invention, a generally elongate housing 510 defines an interior cavity 512 which may be configured for the particular pump or valve application, such as with inlet and outlet passages 514 and 516. A shaft or plunger 60 is disposed in the cavity and lengthwise aligned therewith.

A portion 510a of the housing is configured to have a very close fit with the shaft 60, with just enough space between them to allow the shaft to slide in reciprocating movement back and forth in the cavity. The housing portion 510a is thicker than the resilient sheets used for sphincter seals in previous embodiments, and is preferably made of more rigid material such as glass, sapphire or metal. The seal formed between the housing portion 510a and the shaft, therefore, is not complete and leaks slowly. However, if the pump action is fast enough the leakage is comparatively insignificant and the seal is satisfactory.

The seal of FIG. 21 can be used in place of any sphincter seal previously described in connection with apparatuses of the present invention if the volume of fluid flowing through the apparatus is large compared to the leakage through the seal or the leakage is otherwise deemed unimportant to the operation of the apparatus.

FIGS. 22 and 23 show a top view and side, cross-sectional view respectively of a programming card system for controlling the drive systems of the present invention. The embodiment shown in FIGS. 22 and 23 show only one of many ways of controlling the driving of the shafts or other moveable parts in embodiments of the present invention, such as the amplitude and frequency of the shaft's reciprocating movement. Other means of communicating the "program" to a system controller include switches, including rotary switches, bar code readers, and electronic communication from a programming unit to the driver unit, etc. However, the programming card system of FIGS. 22 and 23 is especially convenient for programming an IV pump controller, such as the control unit 118 of FIG. 3. A physician or pharmacist could readily prepare a card (as will be discussed momentarily) to control the parameters and operational mode of an IV pump as required for a particular patient.

The programming card system of FIGS. 22 and 23 comprises a programming card 520 containing selectively punched holes 522 (punched, for example, by a physician or pharmacist) and index tracks 524. The holes and tracks are arranged in columns and rows. The card is designed for placement in a card reader 526, which comprises a series of conductive fingers 528 which are mounted on and biased against a printed circuit board 529 or equivalent structure which contains traces 530 electrically connected to a control unit or circuit 532. The traces are disposed beneath the portion of the fingers which contacts the board 529, and detect when the fingers contact the board.

In operation, the holes and index tracks in the programming card are aligned with the fingers 528. When the card is fed into the reader 526 the holes, which are selectively chosen on the card, allow contact between the fingers and the traces, while other portions of the card which have not been punched out do not allow the electrical connection to be made, thus allowing the reader to interpret the information on the card and appropriately program the controller for the driver of the apparatus of the present invention.

Figure 24:
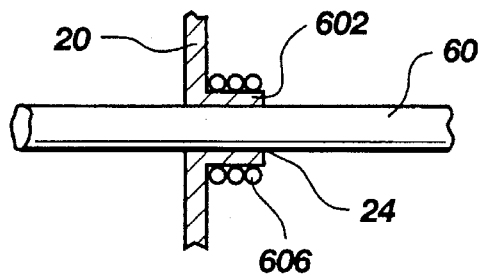
FIG. 24 is a fragmented, side, cross-sectional view of a spring assisted seal arrangement suitable for use in the present invention.

FIG. 24 shows a fragmented, side, cross-sectional view of a sphincter seal, including a shaft 60 disposed in an aperture 24 formed in a sheet of flexible material 20. In this embodiment, a lip 602 of the aperture 24 of the sheet of material 20 is formed to turn inwardly toward the interior of the pump housing (not shown) to effectively lie snugly about a portion of the shaft 60. A coil spring 606 is disposed about the lip 602 to urge the lip tightly against the shaft 60 to further enhance the seal between the sheet of material 20 and the shaft 60.

Figure 25:
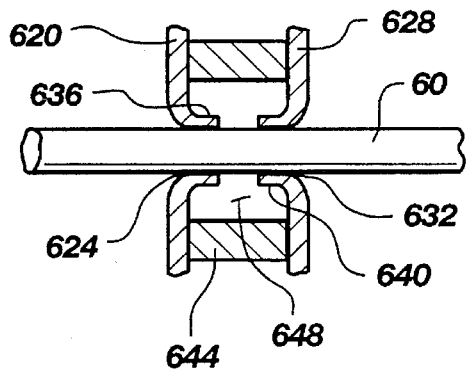
FIG. 25 is a fragmented, side, cross-sectional view of a duplex, inwardly turned sphincter seal arrangement suitable for use in the present invention.

FIG. 25 shows a fragmented, side, cross-sectional view of a duplex sphincter shield arrangement, including a shaft 60, a first flexible sheet of material 620 having an aperture 624 formed therein, and a second sheet of flexible material 628 having an aperture 632 formed therein. A lip 636 of the aperture 624 of the sheet of material 620 is turned inwardly as shown, as is a lip 640 of the aperture 632 of the sheet of material 628, so that the lips are facing inwardly towards one another. A ring 644 is disposed between the sheets of material 620 and 628 to define a substantially airtight cavity 648 between the sheets of material 620 and 628, the ring 644, and the shaft 60.

With the configuration of FIG. 25, when the shaft 60 is moved longitudinally in either direction, the sheets of material 620 and 628 are flexed to increase the pressure in the cavity 648 and force the lip 636 and 640 in tighter contact with the shaft 60.

Figure 26:
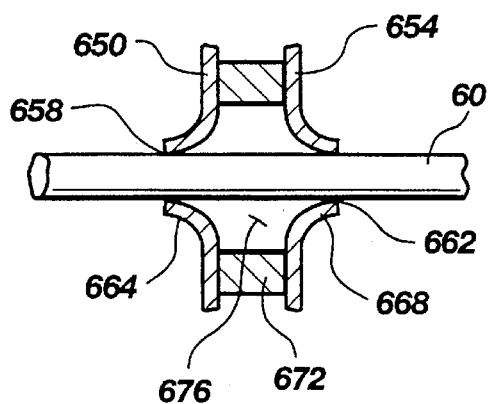
FIG. 26 is a fragmented, side, cross-sectional view of a duplex, outwardly turned sphincter seal arrangement suitable for use in the present invention.

FIG. 26 is a fragmented, side, cross-sectional view of a duplex sphincter seal arrangement again including a shaft 60, a pair of flexible sheets of material 650 and 654, each with apertures 658 and 662 respectively, for receiving the shaft 60. However, instead of lips 664 of the sheet of material 650, and 668 of the sheet of material 654, turning inwardly towards one another as in FIG. 25, the lips are turned outwardly away from one another as shown. A ring 672 is disposed between the sheets of material 650 and 654 to define a cavity 676 similar to the cavity 648 of FIG. 25.

In operation, when the shaft 60 of the seal arrangement of FIG. 26 is reciprocated in either direction, a vacuum is produced in the cavity 676 so that outside pressure acts to force the lips 664 and 668 in tighter contact with the shaft 60, as desired.

The embodiments of the invention described herein are only examples of how the invention may be applied to specific devices. Modifications and variations of, for example, materials used, sizes and shapes of components, and equivalent structures will be apparent to those skilled in the art while remaining within the scope of the invention.

What is claimed is:

1. A volumetric pump and fluid flow control valve system comprising a housing having a central hollow, an inlet and an outlet, both for communicating with the central hollow, and a third opening, a first sheet of resilient material disposed in the housing between the inlet and the central hollow, with an aperture formed in the sheet, a second sheet of resilient material disposed in the housing between the outlet and the central hollow, with an aperture formed in the second sheet, a third sheet of resilient material disposed over the third opening, said third sheet having an opening therein, an elongate valve spool disposed to move longitudinally within the central hollow of the housing between a first position in which the aperture in the first sheet is unplugged and the aperture in the second sheet is plugged, to allow fluid to flow through the inlet into the central hollow, and a second position in which the aperture in the first sheet is plugged and the aperture in the second sheet is unplugged, to allow fluid to flow from the central hollow and out the outlet, an elongate plunger means extending through the aperture in the third sheet of material and into the central hollow for reciprocating back and forth to alternately move farther into the central hollow and then move the valve spool to the first portion, and move farther out of the central hollow and then move the valve spool to the second position, and means for causing the plunger means to reciprocate.

* * * * *

UNITED STATES PATENT AND TRADEMARK OFFICE
CERTIFICATE OF CORRECTION

PATENT NO. : 5,556,263
DATED : SEPTEMBER 17, 1996
INVENTOR(S) : STEPHEN C. JACOBSEN and CLARK C. DAVIS It is certified that error appears in the above-indentified patent and that said Letters Patent is hereby corrected as shown below:

The title should be changed to read:

"VOLUMETRIC PUMP AND VALVE"

Signed and Sealed this

Twenty-fifth Day of February, 1997

Attest:

BRUCE LEHMAN

*Attesting Officer*  *Commissioner of Patents and Trademarks*